United States Patent [19]

Floyd et al.

[11] Patent Number: 4,946,838

[45] Date of Patent: Aug. 7, 1990

[54] CRYSTALLINE ANHYDROUS AZTREONAM

[75] Inventors: David Floyd, Pennington; Octavian R. Kocy, Kendall Park; Donald C. Monkhouse, Princeton; James D. Pipkin, New Brunswick, all of N.J.

[73] Assignee: E. R. Squibb & Sons, Inc., Princeton, N.J.

[21] Appl. No.: 888,640

[22] Filed: Jul. 28, 1986

Related U.S. Application Data

[63] Continuation of Ser. No. 282,636, Jul. 13, 1981, abandoned.

[51] Int. Cl.$^5$ ............... C07D 205/085; A61K 31/395
[52] U.S. Cl. .................................... 514/210; 540/355
[58] Field of Search .................... 540/355; 514/210

[56] References Cited

U.S. PATENT DOCUMENTS

| | | | |
|---|---|---|---|
| Re. 28,744 | 3/1986 | Long et al. | 260/239.1 |
| 2,985,648 | 5/1961 | Doyle | 260/239.1 |
| 3,157,640 | 11/1964 | Johnson | 260/239.1 |
| 3,192,198 | 6/1965 | Nayler | 260/239.1 |
| 3,485,819 | 12/1969 | Weisenborn | 260/239.1 |
| 3,507,861 | 4/1970 | Morin | 260/239.1 |
| 3,655,656 | 4/1972 | Van Heyningen | 260/239.1 |
| 3,819,620 | 6/1974 | Dursch | 260/239.1 |
| 3,905,960 | 9/1975 | Clark | 540/320 |
| 3,932,386 | 1/1976 | Nescio | 540/321 |
| 4,006,138 | 2/1977 | Yang | 540/226 |
| 4,529,698 | 7/1985 | Sykes | 435/822 |

FOREIGN PATENT DOCUMENTS 21678 1/1981 European Pat. Off. .

OTHER PUBLICATIONS

Monkhouse, Drug Development and Industrial Pharmacy, 10, 1373-1392, 1393 (1984).
Physicians Desk Reference, 1986, pp. 302, 305.

*Primary Examiner*—Mark L. Berch
*Attorney, Agent, or Firm*—Timothy J. Gaul

[57] ABSTRACT

The crystalline anhydrous form of [3S-[3α(Z), 4β]]-3-[[(2-amino-4-thiazolyl) [(1-carboxy-1-methylethoxy)imino]acetyl]amino]-4-methyl-2-oxo-1-azetidinesulfonic acid is prepared.

6 Claims, No Drawings

CRYSTALLINE ANHYDROUS AZTREONAM

BACKGROUND OF THE INVENTION

Prior Application

This is a continuation of Ser. No. 282,636, filed 7/13/81, now abandoned.

In U.S. Pat. application, Ser. No. 226,562, filed Jan. 19, 1981, by Richard B. Sykes, et al., there is described a method for preparing the new antibacterial agent, [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, having the formula

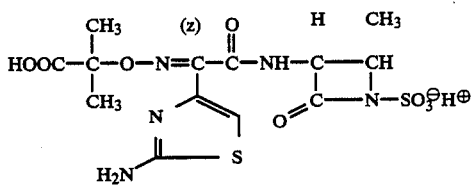

The compound so obtained is in the form of hydrated crystals, which are relatively unstable.

BRIEF DESCRIPTION OF THE INVENTION

This invention is directed to the discovery that [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid can be obtained in a relatively stable, crystalline, anhydrous form by recrystallizing the hydrated crystalline form of the compound from an anhydrous organic solvent. The resulting product is crystalline, anhydrous and substantially non-hygroscopic and has a stability greater than that of the starting material from which it is made.

DETAILED DESCRIPTION OF THE INVENTION

When [3S-[3α(Z),4β]]-3-[[(2-amino-4-thiazolyl) [(1-carboxy-1-methylethoxy)imino]acetyl]amino]-4-methyl-2-oxo-1-azetidinesulfonic acid is prepared as described in U.S. patent application, Ser. No. 226,562, as shown in Preparation A below, the product is obtained in the form of hydrated crystals, which have been designated as the α-form. This α-form of the product is relatively unstable.

It has now been found that if this α-form is recrystallized from an anhydrous organic solvent, a new crystalline form of [3S-[3α(Z),4β]]-3-[[(2-amino-4-thiazolyl)[(1-carboxy-1-methylethoxy)imino]acetyl]amino]-4-methyl-2-oxo-1-acetidinesulfonic acid, which has been designated as the β-form, is obtained. The β-form is anhydrous, substantially non-hygroscopic and more stable than the α-form, as shown in Table 1 below.

Although the β-form of the compound can be prepared simply by dissolving the α-form in an anhydrous organic solvent, such as an alkanol (e.g., methanol and ethanol), it is preferable that the α-form is first converted to a salt, as by treating the α-form of the acid with an amine, such as a tri(lower alkyl)-amine (e.g., triethylamine), in an anhydrous organic solvent and then precipitated therefrom in the β-form by reacting with an acid, such as a mineral acid (e.g., hydrochloric acid). Alternatively the α-form of the acid can be converted to a silyl derivative, as by treating the α-form of the acid with a silylating agent, such as bis-trimethylsilylacetamide, monotrimethylsilylacetamide, bis-trimethylsilyl urea and monotrimethylsilyltrifluoroacetamide, in an aprotic organic solvent and then precipitated therefrom in the β-form by dilution of the solution with ethanol to hydrolyze the silyl derivative.

The α-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid can be prepared as described in the following Preparation A, in which all temperatures are in Centigrade:

PREPARATION A

α-Form of [3S-[3α(Z),4β]]-3-[[(2-Amino-4-thiazolyl) [(1-carboxy-1-methylethoxy)imino]acetyl]amino]-4-methyl-2-oxo-1-azetidinesulfonic Acid

(A) N-Benzyloxy-t-boc-threonine amide

A solution of 8.76 g of t-boc-threonine and the free amine from 6.4 g of O-benzylhydroxylamine HCl (ethyl acetate-sodium bicarbonate liberation) in 100 ml of tetrahydrofuran is treated with 6.12 g of N-hydroxybenzotriazole and 8.24 g of dicyclohexylcarbodiimide in 20 ml of tetrahydrofuran. The mixture is stirred under nitrogen for 26 hours, filtered, and evaporated in vacuo. The residue is chromatographed on a 300 g silica gel column (elution with chloroform and chloroformethyl acetate (3:1)) yielding 7.2 g of compound. Crystallization from ether-hexane gives 4.18 g of the title compound.

(B) (3S-trans)-N-Benzyloxy-3-t-butoxycarbonylamino-4-methylazetidinone

A solution of 12.67 g of N-benzyloxy-t-boc-threonine amide, 11.5 g of triphenylphosphine, and 6.23 ml of diethylazodicarboxylate in 380 ml of tetrahydrofuran is stirred under nitrogen for about 16 hours. The solution is evaporated and chromatographed on a 900 gram silica gel column. Elution with chloroform-ethyl acetate (3:1) gives 13.69 g of compound that crystallizes from ether-hexane to yield 9.18 g of the title compound.

(C) (3S-trans)-3-t-Butoxycarbonylamino-1-hydroxy-4-methylazetidinone

A solution of 9.18 g of (3S-trans)-N-benzyloxy-3-t-butoxycarbonylamino-4-methylazetidinone in 300 ml of 95% ethanol is stirred in an atmosphere of hydrogen with 1.85 g of 10% palladium on charcoal. After 141 minutes the slurry is filtered and evaporated in vacuo. The residue is recrystallized from ether-hexane to yield 5.12 g of the title compound.

(D) (3S-trans)-3-t-Butoxycarbonylamino-4-methylazetidinone

A solution of 4.98 of (3S-trans)-3-t-butoxycarbonylamino-1-hydroxy-4-methylazetidinone in 200 ml of methanol is treated with 132 ml of 4.5 M ammonium acetate and then 66 ml of 1.5 M titanium trichloride and stirred for 4.5 hours. The aqueous solution is diluted with an equal volume of 8% sodium chloride and extracted with ethyl acetate to give 3.48 g of crude product. Recrystallization from ether-hexane yields 3.3 g of the title compound.

(E)
(3S-trans)-3-Benzyloxycarbonylamino-4-methylazetidinone

A solution of 3.3 g of (3S-trans)-3-t-butoxycarbonylamino-4-methylazetidinone in 10 ml each of dichloromethane and anisole is cooled to 0° C. and 112 ml of trifluoroacetic acid is added. The solution is stirred for 90 minutes and evaporated in vacuo (benzene added and evaporated three times). The residue is dissolved in 70 ml of acetone and the solution is adjusted to pH 7 with 5% sodium bicarbonate solution. A total of 5.33 g of benzyl chloroformate is added over 1 hour at pH 6.5–7.5. The mixture is stirred for 30 minutes at pH 7, diluted with 100 ml of saturated salt, and extracted with ethyl acetate (three 400 ml portions). The residue obtained by evaporation is chromatographed on a 1 liter silica gel column. Elution with chloroform-ethyl acetate (4:1) gives 2.19 g of compound. Crystallization from ether-hexane yields 1.125 g of the title compound.

(F) (3S-trans)-4-Methyl-2-oxo 3-[(phenylmethoxy)-carbonyl]amino]-1-azetidinesulfonic acid, tetrabutylammonium salt A solution of 600 mg of (3S-trans)-3-benzyloxycarbonylamino-4-methylazetidinone in 2 ml of dimethylformamide is cooled to 0° C. and 4 ml of 0.8 M sulfur trioxide in dimethylformamide is added. The solution is stirred at room temperature under nitrogen for 1 hour and poured into 80 ml of cold 0.5 M monobasic potassium phosphate (adjusted to pH 5.5). The solution is extracted with three 50 ml portions of methylene chloride (discarded) and 868 mg of tetrabutylammonium bisulfate is added. The resulting solution is extracted with, four 75 ml portions of methylene chloride. The combined organic layer is washed with 8% aqueous sodium chloride, dried, and evaporated in vacuo yielding 1.54 g of the title compound.

(G) [3S-[3α(Z),4β]]-3-[[(2-Amino-4-thiazolyl)-[(1-diphenylmethoxycarbonyl-1-methylethoxy)imino]-acetyl]amino]-4-methyl-2-oxo-1-azetidinesulfonic acid, potassium salt A solution of 1.54 g of (3S-trans)-4-methyl-2-oxo-3-[[(phenylmethoxy)carbonyl]amino]-1-azetidinesulfonic acid, tetrabutylammonium salt in 45 ml of dimethylformamide is stirred in an atmosphere of hydrogen with 800 mg of 10% palladium on charcoal for 2 hours. The catalyst is filtered and the filtrate stirred for about 16 hours with 1.24 g of (Z)-2-amino-α-[(1-diphenylmethoxycarbonyl-1-methylethoxy)imino]-4-thiazoleacetic acid, 0.4 g of N-hydroxybenzotriazole, and 580 mg of dicyclohexylcarbodiimide. The slurry is evaporated in vacuo and the residue is triturated with 20 ml of acetone and filtered. The filtrate (plus 2 ml of washings) is treated with 868 mg of potassium perfluorobutanesulfonate in 3 ml of acetone. Dilution with 75 ml of ether gives a solid that is isolated by decantation of the mother liquor, trituration with ether, and filtration to give 0.91 g of the title compound. The mother liquor is diluted with a further 100 ml of ether to give a second crop, 0.45 g, of the title compound.

(H) [3S-[3α(Z),4β]]-3-[[(2-Amino-4-thiazolyl)[(1-carboxy-1-methylethoxy)imino]-acetyl]amino]-4-methyl-2-oxo-1-azetidinesulfonic acid, dipotassium salt A slurry of 140 mg of [3S-[3α(Z),4β]]-3-[[(2-amino-4-thiazolyl)[(1-diphenylmethoxycarbonyl-1-methylethoxy)imino]acetyl]amino]-4-methyl-2-oxo-1-azetidinesulfonic acid, potassium salt (first crop) in 0.5 ml of anisole is stirred at −12° C. under nitrogen and 2.5 ml of cold (−10° C.) trifluoroacetic acid is added. After 10 minutes, 10 ml of ether and 5 ml of hexane are added and the resulting slurry is stirred for 5 minutes at −12° C., and allowed to warm to room temperature. The solid is isolated by centrifugation and washed twice with ether. A solution of this solid in 5 ml of cold water is immediately adjusted to pH 5.5 with 0.4 N potassium hydroxide and then applied to an 80 ml HP-20 AG column. Elution with water gives 72 mg of the title compound in fractions (10 ml) 7–11 after evaporation (acetonitrile added and evaporated three times) and trituration with ether.

Analysis calc'd for $C_{13}H_{15}N_5O_8S_2K_2$: C, 30.51; H, 2.95; N, 13.69; S, 12.53; K, 15.28

Found: C, 29.63; H, 3.20; N, 12.96; S, 11.94; K, 12.78

The remaining 1.22 g of [3S-[3α(Z), 4β]]-3-[[(2-amino-4-thiazolyl)[(1-diphenylmethoxycarbonyl-1-methylethoxy)imino]acetyl]amino-4-methyl-2-oxo-1-azetidinesulfonic acid, potassium salt (crops 1 and 2) are treated, as above (4.2 ml anisole, 16 ml of trifluoroacetic acid, 13 minutes at −15° C.). Chromatography on a 300 ml HP-20AG column gives 694 mg of the title compound in fractions (60 ml) 6–9 after treatment as above.

(I) α-Form of [3S-[3α(Z),4β]]-3-[[(2-amino-4-thiazolyl)-[(1-carboxy-1-methylethoxy)imino]acetyl]amino]-4-methyl-2-oxo-1-azetidinesulfonic acid

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid, dipotassium salt (87.3 mg) is dissolved in 1.38 ml of water, cooled to 0° C., treated with 0.34 ml of 1N hydrochloric acid and the resulting crystals separated by centrifugation. The wet solid is dissolved in methanol, filtered, concentrated to about 0.5 ml and mixed with 1 ml of water, giving 55.9 ml of the title compound.

The preparation of the β-form from the α-form can be accomplished by any one of the procedures set forth in the following Examples, in which all temperatures are in Centigrade:.

EXAMPLE 1

β-Form of [3S-[3α(Z),4β]]-3-[[(2Amino-4-thiazolyl) [(1-carboxy-1-methylethoxy)imino]acetyl]amino]-4-methyl-2-oxo-1-azetidinesulfonic Acid A sample of 1.73g of the α-form of [3S-[3a(Z), 4β]]-3-[[(2-amino-4-thiazolyl)[(1-carboxy-1-methylethoxy)imino]acetyl]amino]-4-methyl-2-oxo-1-azetidinesulfonic acid is recrystallized from 40ml of methanol-water (1:1). The resulting purified α-form is filtered, washed with dichloromethane and acetone, and air dried. The solid is redissolved in methanol (20ml - slight heating). Crystallization occurs and is completed at −20° for 4 days. The solid is filtered and washed with dichloromethane to give about 1.18g of β-form of [3S-[3α(Z),4β]]-3-[[(2-amino-4-thiazolyl)[(1-carboxy-1- methylethoxy) imino]acetyl]amino]-4-methyl-2-oxo-1-azetidinesulfonic acid (verified by differential scanning calorimetry).

EXAMPLE 2

A slurry of 403 mg of the α-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid in 8ml of acetonitrile is treated with 0.75 ml of bis-trimethylsilylacetamide at 45° to give a clear solution. This solution is added to 16 ml of absolute ethanol, seeded with the β-form of [3S-[3α(Z),4β]]-3-[[(2-amino-4-thiazolyl) [(1-carboxy-1-methylethoxy)imino]acetyl]amino]-4-methyl-2-oxo-1-azetifinesulfonic acid, and stirred for 150 minutes. The resulting solid is filtered, washed with ethanol, and dried in vacuo overnight to give about 100 mg of the β-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid (verified by X-ray powder diffraction).

EXAMPLE 3

A slurry of 1.742 g of the α-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid (14% $H_2O$, 0.00345 mole) in 20 ml of absolute ethanol is stirred at room temperature and 0.557 ml (0.004 mole) of triethylamine added. After 10 minutes a clear solution forms. Addition of 0.476 ml of 8.4N ethanolic HCl, followed by seeding the solution with the β-form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid produces a slurry. This is stirred for 90 minutes. filtered, and air dried to give about 1.416 g (94%) of the β-form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid (verified by differential scanning calorimetry).

EXAMPLE 4

A sample of 10 g of the α-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid is slowly added to 100 ml of absolute methanol at 55°. Dissolution, cooling and crystallization occur simultaneously. The solid is filtered and air dried to give about 8 g of β-form of [3S-[3α(Z),4β8]]-3-[[(2-amino-4-thiazolyl)[(1-carboxy-1-methylethoxy)imino]acetyl-] amino]-4-methyl-2-oxo-1-azetidinesulfonic acid (verified by differential scanning calorimetry).

EXAMPLE 5

A sample of 50 g of the α-form of [3S-[3α(Z), 4β]]-3-[[(2-amino-4-thiazolyl)[(1-carboxy-1-methylethoxy)imino]acetyl]amino]-4-methyl-2-oxo-1-azetidinesulfonic acid is recrystallized from 670 ml of methanol-water (7:1). The resulting purified α-form is filtered and the wet cake added to absolute ethanol at 50° with manual glass rod stirring. The suspension is cooled to room temperature and the solid is filtered and air dried to give about 37 g of β-form of [3S-[3α(Z), 4β]]-3-[[(2-amino-4-thiazolyl)[(1-carboxy-1-methylethox-y)imino]acetyl]amino]-4-methyl-2-oxo-1-azetidinesulfonic acid (verified by X-ray powder diffraction).

EXAMPLE 6

To 40 ml of ethanol, preheated to 60° is added 4.9 g of the α-form of [3S-[3α(Z),4β]]-3-[[(2-amino-4-thiazolyl)[(1-carboxy-1-methylethoxy)-imino]acetyl]amino-4-methyl-2-oxo-1-azetidine-sulfonic acid (9% $H_2O$). The α-form dissolves momentarily, then recrystallizes spontaneously as the β-form. The hot mixture is cooled to 20° to 25°, stirred for one hour and filtered. The crystals are dried to give about 4.0 g of the β-form of [3S-[3α(Z),4β]]-3-[[(2-amino-4-thiazolyl)[(1-carboxy-1-methylethoxy)imino]acetyl]amino-4-methyl-2-oxo-1-azetidinesulfonic acid (verified by X-ray powder diffraction and differential scanning calorimetry).

The β-form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid can be characterized as a stable, dense, anhydrous, crystalline, nonhygroscopic granular powder, exhibiting characteristic X-ray powder diffraction curves that distinguish it from the α-form. Thus, the curves of the α-form typically show a drifting baseline, broader and less intense peaks than the straight baseline, sharper and more intense peaks typical of curves of the β-form. The following is a listing of interplanar distances ('d') versus intensity (I) of the alpha and beta forms, the intensity being expressed as % of full scale (F.S.), where off-scale peaks are expressed as >100:

|  | β-Form | | | |
|---|---|---|---|---|
| α-Form | | Sample I | | Sample II |
| 'd' (Å) | I (% F.S.) | 'd' | I (% F.S.) | 'd' | I (% F.S.) |
| 3.2 | 7 | 3.18 | 40 | | |
| 3.26 | 34 | 3.23 | 58 | 3.21 | 29 |
| 3.32 | 25 | 3.35 | 35 | 3.32 | 18 |
| 3.43 | 60 | 3.43 | 35 | 3.43 | 16 |
| 3.67 | 28 | 3.5 | 5 | | |
| 3.74 | 35 | 3.62 | 60 | 3.60 | 32 |
| 3.90 | 32 | 3.72 | 45 | | |
| 3.98 | 25 | 3.8 | 60 | 3.78 | 39 |
| 4.22 | 21 | 3.87 | 10 | | |
| 4.37 | 7 | 4.12 | >100 | 4.10 | >100 |
| 4.47 | 10 | 4.23 | >100 | 4.20 | >100 |
| 4.6 | 30 | 4.41 | 15 | 4.40 | 11 |
| 4.7 | 57 | 4.72 | >100 | 4.72 | >100 |
| 5.03 | 26 | 4.90 | 20 | 4.50 | 16 |
| 5.32 | 48 | 5.0 | 55 | 4.95 | 35 |
| 5.64 | 7 | 5.25 | >100 | 5.21 | >100 |
| 5.82 | 32 | 5.4 | 5 | | |
| 6.35 | 6 | 5.62 | 23 | 5.6 | 18 |
| 6.7 | 12 | 5.78 | 25 | 5.75 | 15 |
| 7.0 | >100 | 6.32 | 15 | 6.3 | 10 |
| 7.1 | 33 | 7.8 | >100 | 7.7 | >100 |
| 8.1 | 10 | 9.3 | 20 | 9.2 | 14 |
| 9.2 | 30 | 10.0 | 40 | 9.9 | 29 |
| 10.7 | 35 | | | | |
| 13.8 | 20 | | | | |
| 18.9 | >100 | | | | |

Note that the peak intensities may change subject to variation in sample preparation.

The β form of [3S-[3α(Z),4β]]-3-[[(2-amino-4-thiazolyl) [(1-carboxyl-1-methylethoxy)imino]acetyl]amino]-4-methyl-2-oxo-1-azetidinesulfonic acid can also be distinguished from the β-form from which it is made as shown in the following Table:

TABLE 1

Physical and Processing Properties of Crystalline Forms of [3S-[3α(Z),4β]]-3-[[(2-Amino-4-thiazolyl) [(1-carboxy-1-methylethoxy)imino]acetyl]amino]-4-methyl-2-oxo-1-azetidinesulfonic Acid

| Property | α-Form | β-Form |
|---|---|---|
| Hydration: | Hydrous (7-14% water) | Anhydrous (0-1% water) |
| Crystallinity: | | |
| Microscopy | birefringent | birefringent |
| X-ray diffraction | crystalline | crystalline |
| $^1$DSC, peak temperatures: | | |
| exotherm | 200° C. (decomp.) | 238° (decomp) [when crystallized from absolute methanol] 228° (decomp) [when crystallized from absolute ethanol] |
| endotherm | 107° C. (dehydration) | none |
| Morphology | needles or rods | spiny fused spherulites |
| Hygroscopicity: | | |
| $^2$EMC | 0-14% | 0-3% |
| Rate | rapid | slow |
| Infrared Spectra: | very wide absorption band in the 3000-3600 cm$^{-1}$ region (characteristic of water); poorly resolved shoulder on the peak at 1650 cm$^{-1}$ (carbonyl region). | narrower band in the 3000-3600 cm$^{-1}$ region; well resolved shoulder on the peak at about 1780 cm$^{-1}$. |
| Density | low | high |
| Surface Area | high | low |
| Flowability | poor | good |
| Intrinsic Dissolution Rate | slow | fast |
| Solid State Stability | poor | good |
| Ease of Manufacture (Aseptic Powder Blend) | poor | good |

$^1$DSC - Differential Scanning Calorimetry
$^2$EMC - Equilibrium Moisture Content Because of its increased stability, the β-form of the compound is particularly well suited for use as a pharmaceutical agent. Since [3S-[3α(Z),4β]]-3-[[(2-amino-4-thiazolyl)[(1-carboxy-1-methylethoxy) imino]acetyl]amino]-4-methyl-2-oxo-1azetidinesulfonic acid is preferably administered parenterally, the medicament can be marketed as a powder for reconstitution to be mixed with sterile water prior to injection. The shelf life of the β-form, because of its enhanced stability, is greater than that of the α-form, or for that matter simple salts of the compound, thereby permitting more prolonged storage prior to reconstitution, without material decomposition. This is a meaningful advantage of, the β-form when utilized commercially.

Although the powder for reconstitution could theoretically contain only the β-form of the compound, it preferably is a dry mixture of the β-form of the compound with a basic material, so that upon reconstitution, the resulting composition represents a true solution having a pH in the desired range of about 4 to about 8. Among the basic materials that can be mixed with the β-form of the compound to yield the desired powder for reconstitution may be mentioned salts of strong bases with weak acids, such as the alkali metal (e.g., sodium carbonate, sodium bicarbonate and sodium dibasic phosphate); aminoacids, such as L-arginine; and amines, such as meglumine. The blend preferably contains about 1.4 to about 2.2 moles of the basic material per mole of the β-form of the compound.

The following Example shows the preparation of a blend of the β-form of the compound with L-arginine:

EXAMPLE 7

A sample of 1 kg of the β-form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid and from 550 to 900 g of L-arginine or 1.4 to 2.2 moles of another suitable base is placed in a suitable mechanical blender. Processing time is optimized to give a homogeneous blend. The blend is subdivided and the proper amount dispensed into vials and sealed to maintain sterility.

To prepare an injectable solution, one gram of the blend prepared by the procedure of Example 7 is dissolved in 24 ml of sterile water for injection. About 3.5 ml of the resulting solution is then injected intravenously or intramuscularly into a patient having a susceptible gram-negative infection.

What is claimed is:

1. A dry mixture of the crystalline, anhydrous form of [3S-[3α(Z), 4β]]-3-[[(2-amino-4-thiazolyl)[(1-carboxy-1-methylethoxy) imino]acetyl]amino]-4-methyl-2-oxo-1-azetidinesulfonic acid and a basic material.

2. The mixture of claim 1, wherein the basic material is an amine.

3. A dry mixture of the crystalline, anhydrous form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid and the salt of a strong base and a weak acid.

4. A dry mixture of the crystalline, anhydrous form of [3S-[3α(Z),4β]]-3-[[(2-amino-4-thiazolyl)[(1-carboxy-1-methylethoxy)imino]acetyl]amino]-4-methyl-2-oxo-1azetidinesulfonic acid and an aminoacid.

5. The mixture of claim 4, wherein the aminoacid is L-arginine.

6. The mixture of claim 5, wherein about 1.4 to about 2.2 moles of L-arginine are present per mole of the crystalline, anhydrous form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid.

* * * * *